US00PP15542P2

(12) United States Plant Patent
Brits

(10) Patent No.: US PP15,542 P2
(45) Date of Patent: Feb. 8, 2005

(54) ***PLECTRANTHUS* PLANT NAMED 'P000607'**

(50) Latin Name: *Plectranthus hybrida*
Varietal Denomination: P000607

(76) Inventor: Gert Johannes Brits, 28, Flamingo Road, ZA-7600 Stellenbosch (ZA)

( * ) Notice: Subject to any disclaimer, the term of this patent is extended or adjusted under 35 U.S.C. 154(b) by 0 days.

(21) Appl. No.: 10/716,658

(22) Filed: Nov. 20, 2003

(51) Int. Cl.[7] ..... A01H 5/00
(52) U.S. Cl. ..... Plt./263
(58) Field of Search ..... Plt./373, 263

*Primary Examiner*—Anne Marie Grunberg
*Assistant Examiner*—June Hwu
(74) *Attorney, Agent, or Firm*—Foley & Lardner, LLP

(57) ABSTRACT

A new and distinct cultivar of *Plectranthus* plant named 'P000607', characterized by having more compact, freely branching plant habit; shorter production time; vigorous growth habit; large blue flowers; and dense colorful foliage.

3 Drawing Sheets

Latin name of genus and species of the plant claimed: *Plectranthus hybrida.*
Variety denomination: P000607.

BACKGROUND OF THE INVENTION

The present invention relates to a new and distinct cultivar of *Plectranthus* plant, botanically known as *Plectranthus hybrida* (Family Lamiaceae), hereinafter referred to by the name 'P000607'.

The new *Plectranthus*, 'P000607', is a product of a planned breeding program conducted by the Inventor, Gert Johannes Brits, in Stellenbosch, Republic of South Africa. The objective of the breeding program is to improve upon the *Plectranthus* varieties currently available, such as the cultivar 'Edelbau' (unpatented) by developing a *Plectranthus* variety with a more compact growth habit, larger flowers and improved vigor. The new *Plectranthus* originated from a hybrid backcross by the Inventor between a proprietary selection of *Plectranthus* named 'F1' (*P. saccatus*×*P. hilliardiae;* unpatented) and a proprietary selection of unnamed *Plectranthus hilliardiae* (unpatented). The parental cultivar, *P. hilliardiae,* has a compact plant habit, large elongated leaves, purple veined leaves on the underside, and a narrow, elongated flower tube. The parent cultivar P. 'F1' has a tall, straggly plant habit, the leaves are not elongated, green leaves on the underside, and large, wide flower tube, largest flower in the genus.

The new cultivar has been produced only by vegetative propagation (cuttings). The Inventor selected the new *Plectranthus* cultivar from the progeny of the above cross in 2001 on the basis of its compact growth habit; larger flowers and increased vigor.

Asexual reproduction of the new cultivar by terminal cuttings taken and propagated in 1999–2001, has shown that each of the progenies exhibit characteristics identical to the original plant. These characteristics have been shown to come true to form through many generations of asexual propagation under commercial production conditions in Nr. Lyndelse, Fyn, Denmark. The present invention has been tested under lighted greenhouse conditions and for keeping quality in a consumer environment, but may differ in various aspects if grown under different conditions.

SUMMARY OF THE INVENTION

Plants of the cultivar 'P000607' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'P000607'. These characteristics in combination distinguish 'P000607' as a new distinct cultivar:

1. Large blue flowers;
2. Compact and freely branching plant habit;
3. Shorter production time, 12–14 weeks as compared to 16–28 weeks in similar varieties;
4. Dense, colorful foliage; and
5. Sexual sterility.

Side-by-side comparisons between the instant plant and other similar *Plectranthus*, including the variety 'Edelblau', were conducted by the Inventor. Plants of 'P000607' differ from other similar *Plectranthus* cultivars, including the variety 'Edelblau', in the following characteristics:

1. Plants of 'P000607' have longer, clear bright blue flowers than plants of similar *Plectranthus* cultivars.
2. Plants of 'P000607' have better branching growth habit and denser, more colorful foliage than plants of similar *Plectranthus* cultivars.
3. Plants of 'P000607' have a faster growth rate than plants of similar *Plectranthus* cultivars.

BRIEF DESCRIPTION OF THE DRAWINGS

The accompanying photographic drawings illustrate the overall appearance of the new cultivar, showing the colors as true as it is reasonably possible to obtain in colored reproductions of this type. Colors in the photographs may differ slightly from the color values cited in the detailed botanical description, which more accurately describe the actual colors of 'P000607'.

The first photographic drawing shows a side perspective view of a typical flowering plant of 'P000607' as grown in 12 cm pots.

The second photographic drawing shows a close-up view of typical flowering racemes of 'P000607'.

The third photographic drawing shows a close-up of the inflorescence of 'P000607'.

DETAILED BOTANICAL DESCRIPTION

In the following description, color references are made to The Royal Horticultural Society (R.H.S.) Colour Chart, $4^{th}$ edition. Plants were grown under greenhouse conditions. The plants described were between 12 and 15 weeks old after cutting, as grown in 12 cm pots.

Parentage: Hybrid backcross between proprietary selection of *Plectranthus* named 'F1' (*Plectranthus saccatus*×*P. hilliardiea;* unpatented) and unnamed *Plectranthus hilliardiea* (unpatented).

Propagation: Type cutting. Terminal vegetative cuttings.

Plant description:

*Form.*—Perennial, herbaceous plant with upright, branched plant form.

*Crop time.*—Flowering induced by short day treatment in 12 cm pots for 4 weeks under greenhouse conditions.

*Plant height* (*soil level to top of plant plane*).—About 35 cm.

*Plant spread.*—About 35 cm.

*Stem.*—Upright, stiff, square, branching from base, RHS 138 B (dark green).

*Vigor.*—Vigorous growth rate.

*Foliage description.*—Leaves single, ovate, serrate. Arrangement: opposite, decussate. Length: 8 cm. Width: 6 cm. Apex: Acuminate. Base: Cuneate. Texture: adaxial: rough (hispid), shiny; abaxial: smooth, velvety. Venation: prominent, dark purple, N79 B. Color, ventral side: Young foliage, upper and lower surfaces: RHS 136 B, green. Mature foliage, upper and lower surfaces: RHS 139 A. Color, dorsal side: Young foiliage, R.H.S. 139 B. Mature foliage: RHS 138 B.

*Petiole.*—3 mm in length, 5 mm in diameter; hispid texture, N 79 B.

Flower description:

*Flower arrangement.*—Raceme of panicles.

*Flower shape.*—Irregular labiate, flat tubular with 4 lips of different size and shape.

*Flower longevity on the plant.*—Longevity of individual flowers is highly dependent on temperature and light conditions; single flowers last from 4 to 6 days in the greenhouse with full sun and temperatures not exceeding 20° C.; plant may retain flowers up to 4 weeks in sufficient light and temperatures not exceeding 20° C.

*Number of flowers per inflorescence.*—25–30; 80–90 per stem; up to 200 per plant.

*Inflorescence size.*—25–30 flowers per inflorescence: Length (average): 8 cm; Diameter: 6 cm.

*Floral tube.*—Length 23 mm; Diameter (average): 5.5 mm.

*Buds.*—Length: Up to 25 mm before antithesis; height: 5 mm; width: 1 mm; tubular with angular "head", N89 B; base N82B; inner color very light purple, RHS 76D.

*Petals.*—5 fused to basal, flat tubular corolla. Lips spotted, velvety texture. Top lip (2 fused) to inverted cordate form, revolute upright, 15 mm. Bottom lip involute, almost cup-shaped, 7 mm. Wing lips small, rounded, 4 mm. Color: ventral side of lips: light purple, N82D; dark purple spots: N79A; throat: violet, RHS 84 D; dorsal side: blue, RHS 90 C.

*Sepals.*—Lenth 2 mm; width 1 mm, matte texture, puberulent.

*Calyx.*—5 pointed lobes fused at base; veins: dark purple, N79A; ground tissue: green, RHS 136 C.

*Peduncle.*—6 mm length, 3 mm diameter, color RHS N79A.

*Pedicle.*—6 mm length, 1 mm diameter, color RHS N79A.

Reproductive organs:

*Stamen.*—4 monoadelphous, lower part fused to corolla tube.

*Anther.*—Kidney-shaped, 0.25 mm in length, purple, N79B.

*Filaments.*—6 mm in length.

*Pollen.*—Plenty produced, RHS N79B.

*Pistil.*—1, lower part fused to corolla tube; free part 5 mm, curling upward with cleft stigma, purple, N79B.

*Ovary.*—N144A, yellow-green.

*Seed.*—5 seeds per capsule; length and width 1 mm. Immature seeds: RHS 150 B (light yellow-green).

*Fragrance.*—None.

Weather tolerance: Plants of the new *Plectranthus* have exhibited good tolerance to drought, rain and wind, low temperature resistant to 5° C.

I claim:

1. A new and distinct cultivar of *Plectranthus* plant named 'P000607', as illustrated and described herein.

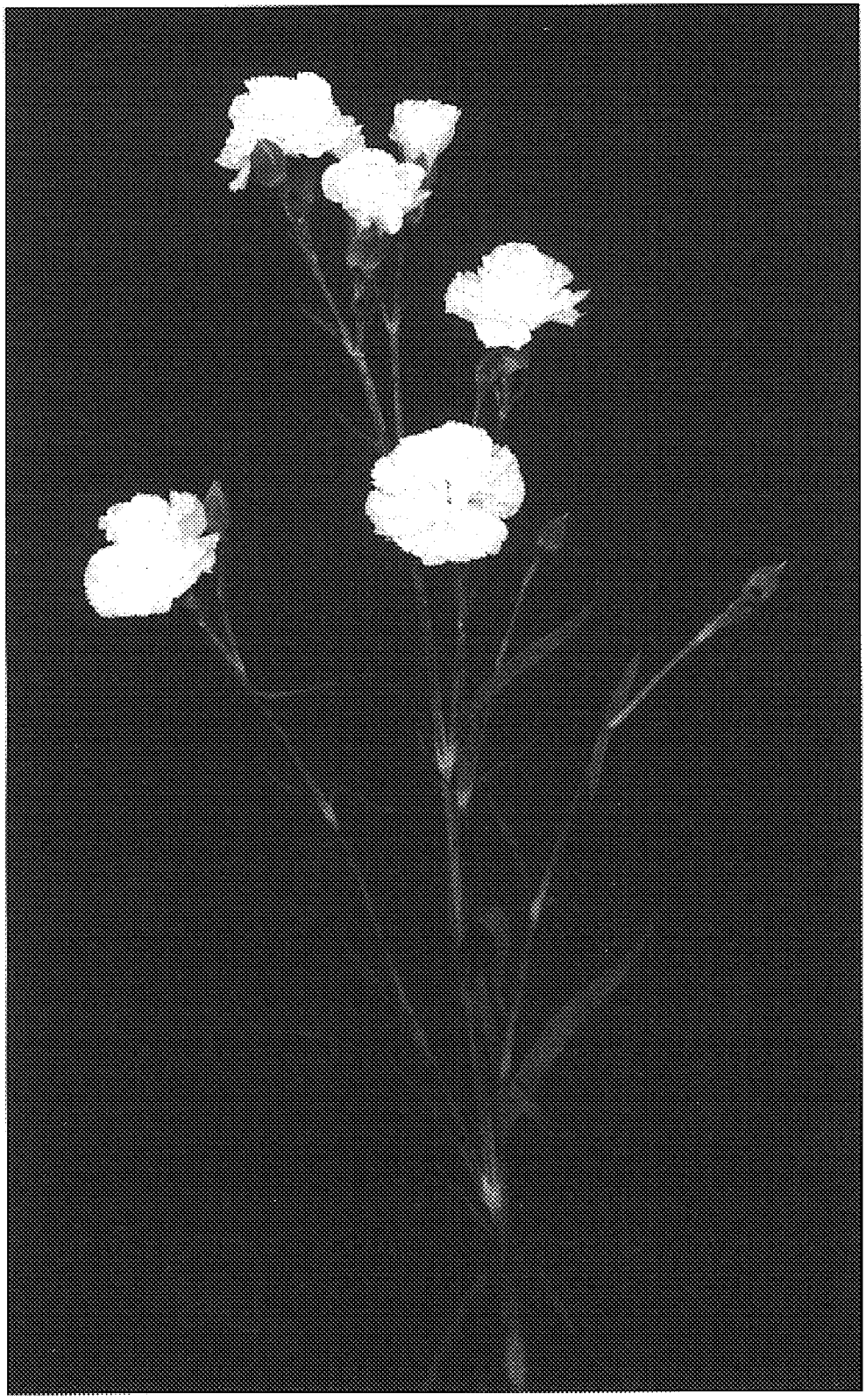

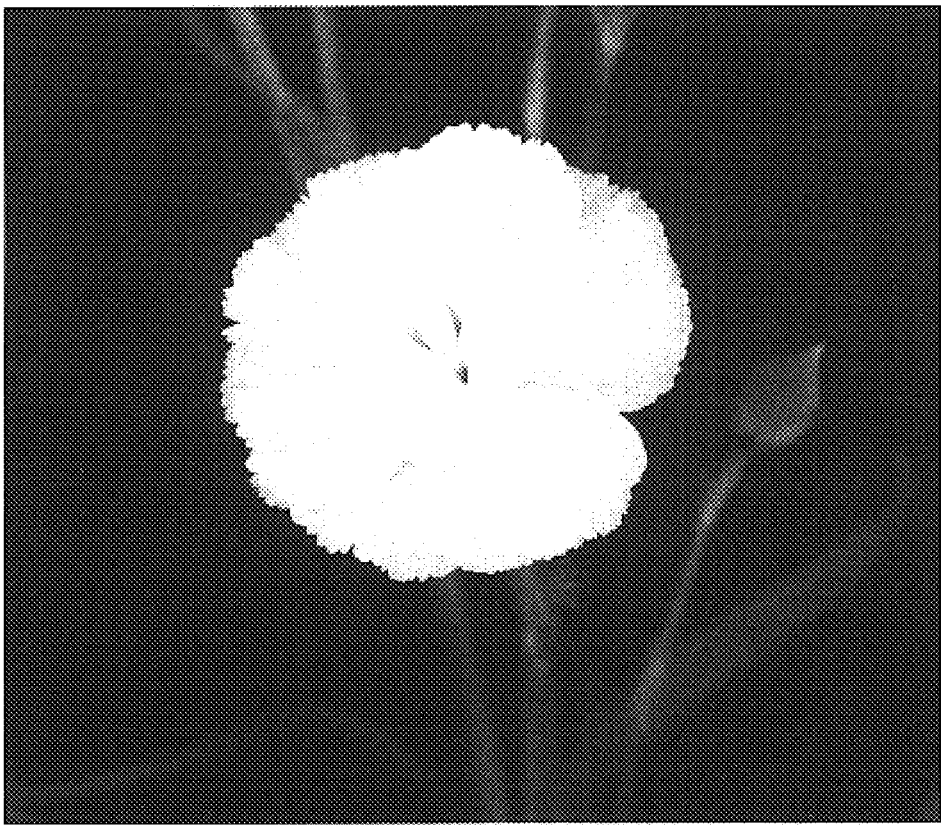

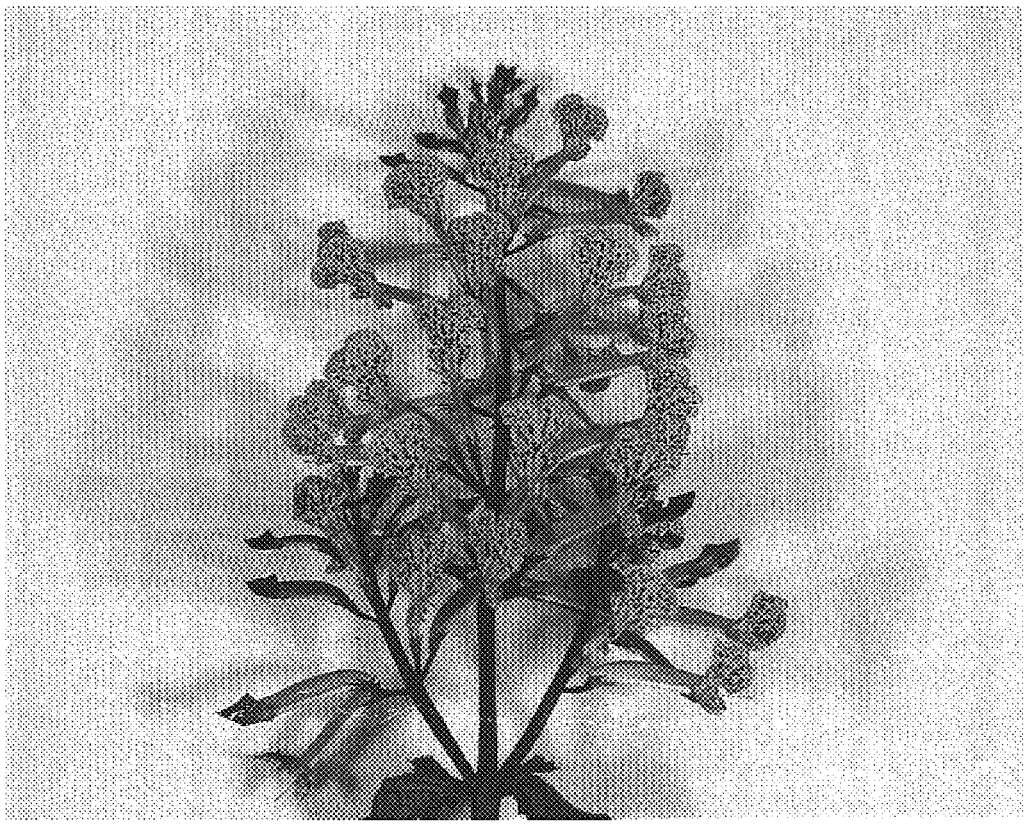

* * * * *